United States Patent [19]

Simpson

[11] Patent Number: 4,616,652
[45] Date of Patent: Oct. 14, 1986

[54] DILATATION CATHETER POSITIONING APPARATUS

[75] Inventor: John B. Simpson, Palo Alto, Calif.

[73] Assignee: Advanced Cardiovascular Systems, Inc., Mountain View, Calif.

[21] Appl. No.: 543,345

[22] Filed: Oct. 19, 1983

[51] Int. Cl.$^4$ ............................................. A61M 29/02
[52] U.S. Cl. .................................... 128/344; 128/657; 128/658; 128/772; 604/280
[58] Field of Search .................... 128/344, 343, 348.1, 128/656, 657, 658, 772, 341, 207.15; 604/96, 104, 107, 282, 280, 281, 164, 171

[56] References Cited

U.S. PATENT DOCUMENTS

| | | | |
|---|---|---|---|
| 3,435,826 | 4/1969 | Fogarty | 128/348 |
| 3,796,211 | 3/1974 | Kohl | 604/171 |
| 4,271,839 | 6/1981 | Fogarty et al. | 128/344 |
| 4,275,724 | 6/1981 | Behrstock | 604/281 |
| 4,323,071 | 4/1982 | Simpson et al. | 128/343 |
| 4,338,942 | 7/1982 | Fogarty | 128/344 |
| 4,363,323 | 12/1982 | Geiss | 604/281 |
| 4,471,776 | 9/1984 | Cox | 128/207.15 |

OTHER PUBLICATIONS

Simpson et al., "A New Catheter System for Coronary Angioplasty," *The American Journal of Cardiology,* vol. 49, (Apr. 1, 1982), pp. 1216–1222.

U.S.C.I., "Percutaneous Catheter Introducer-Venous", *Safety Spring Guides* catalogue, Jun., 1974, p. 8.

*Primary Examiner*—Robert P. Swiatek
*Assistant Examiner*—Cary E. Stone
*Attorney, Agent, or Firm*—Flehr, Hohbach, Test, Albritton & Herbert

[57] ABSTRACT

An insertion guide for a balloon catheter. The insertion guide includes an outer guide tube that defines a passage having an inside diameter sufficient to receive the balloon catheter therethrough. Telescopically receivable within the guide tube is an introducer which defines a lumen centrally thereof. A guide wire is telescoped within the lumen. The guide tube is introduced into a blood vessel by sequentially advancing the guide wire, the introducer and the tube until the distal extremity of the tube is positioned adjacent a stenosis after which the introducer and guide wire are removed. The guide tube has a corrugated wall portion which retains the passage therein in an open condition even when the guide tube assumes an arcuate configuration in traversing an intersection between two blood vessels. Accordingly, the balloon catheter can be introduced, and substantial axial force applied to the proximal extremity thereof is transmitted to the distal extremity to facilitate introduction of the balloon catheter into a stenosis.

12 Claims, 5 Drawing Figures

U.S. Patent  Oct. 14, 1986  4,616,652
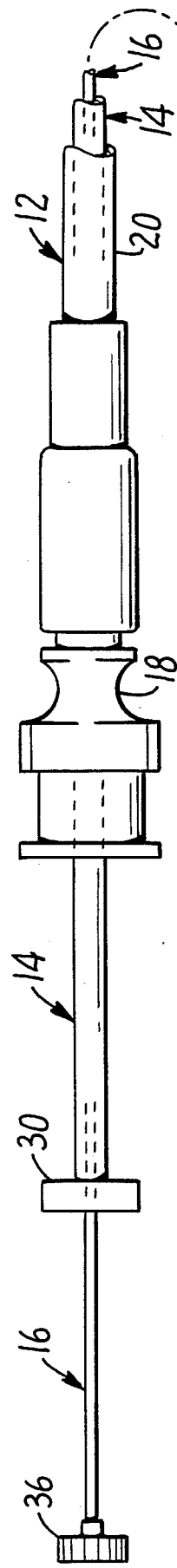
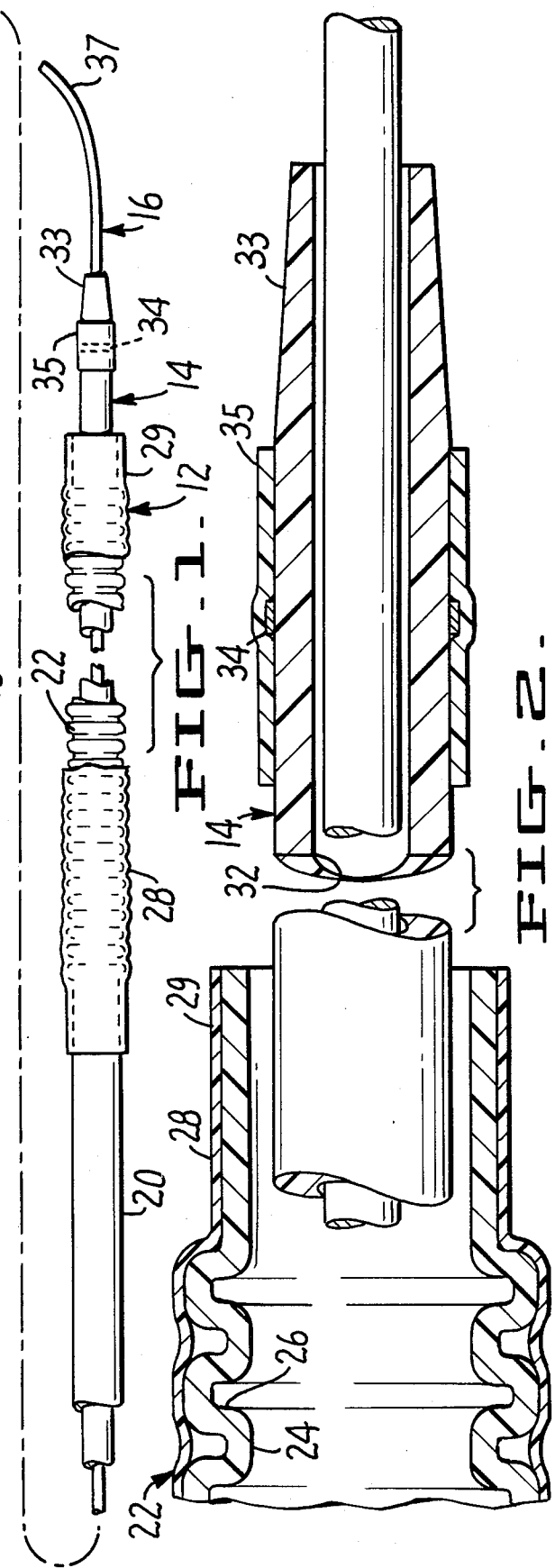
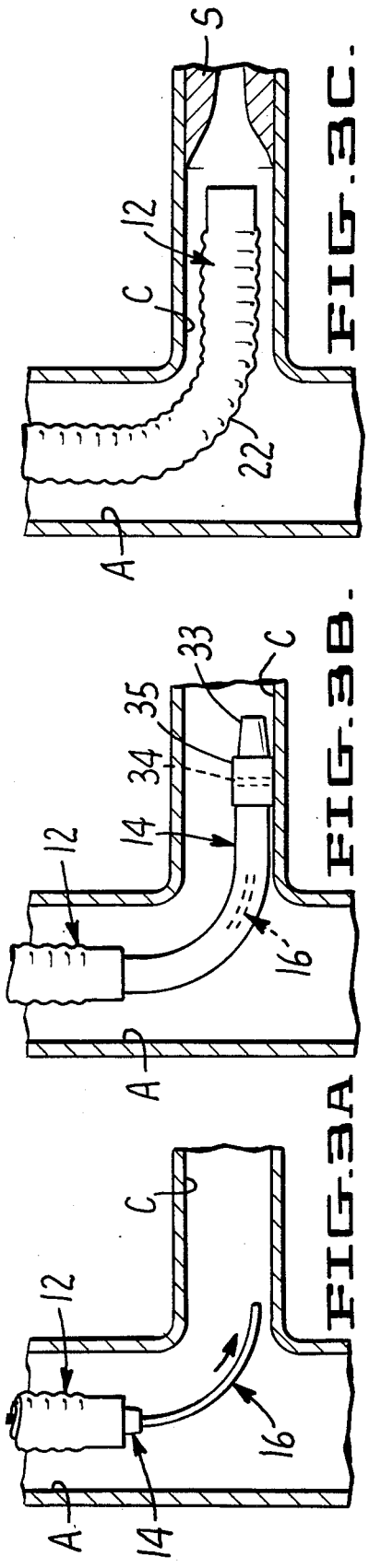

DILATATION CATHETER POSITIONING APPARATUS

BACKGROUND OF THE INVENTION

1. Field of the Invention

This invention relates to apparatus for positioning a dilatation catheter during angioplasty and more particularly to apparatus that affords accurate positioning of the dilatation catheter in any selected coronary blood vessel.

2. Description of the Prior Art

The following United States patents disclosed various forms of dilatation catheters: U.S. Pat. Nos. 3,435,426; 4,271,839; 4,323,071 and 4,338,942. An article titled "A New Catheter System for Coronary Angioplasty" by Simpson et al, *The American Journal of Cardiology*, page 1216 (Apr. 1, 1982), contains a comprehensive description of the angioplasty procedure and describes a guiding catheter having a distal tip that can be shaped to facilitate positioning or guiding a catheter into a selected coronary blood vessel. As mentioned in *The American Journal of Cardiology* reference, the positioning of a dilatation catheter into the left anterior descending or left circumflex coronary artery requires substantial care and dexterity because such arteries intersect the main artery at a rather sharp angle.

SUMMARY OF THE INVENTION

Successful angioplasty requires that the balloon of a dilatation catheter be positioned within a stenosis. The more severe the stenosis, the more pressure required to position the dilatation catheter within it. Although very few stenoses within the main coronary artery are so severe as to be impenetrable by a balloon catheter, about 30% of stenoses located in the left circumflex artery cannot be treated with angioplasty. Such is the case because transmission of axial force to the distal end of the catheter from the proximal end is impeded by presence of a sharp bend where the catheter shaft traverses the intersection of the circumflex artery with the main artery. With an introducer and guide according to the present invention, a tube of substantial structural strength can be positioned in the intersection to afford transmission of force axially of the dilatation catheter.

The present invention provides an introducing guide for a balloon catheter. The guide is composed of three parts that are relatively axially movable in telescoping relation to one another.

The inner-most part is formed of wire the distal end of which can be selectively deformed to facilitate the manipulation of the distal end through blood vessel intersections. The center or intermediate part, which has a central lumen in which the wire is telescoped, has a tapered distal end and is formed of material possessing sufficient rigidity to be advanced along the wire after the wire is in place, and sufficient flexibility to conform to the wire configuration. The outer part telescopes on to the exterior of the intermediate part. The outer part defines a passage having an inside diameter that is large enough to afford entry of a balloon catheter therethrough. The outside diameter of the intermediate part is less than the inside diameter of the passage so that when the wire and intermediate part are positioned, the outer tube can be advanced therealong. The walls of the outer tube are corrugated so that even after the inner guide and wire are removed, preparatory to introducing the dilatation catheter, the outer tube will not kink and will retain a passage of substantially circular cross section so as to afford introduction of the dilatation catheter.

An object of the invention is to provide an introducer for a dilatation catheter that has sufficient flexibility to be manipulated around irregular paths, such as occur within the intersection between the main artery and the left circumflex artery but has sufficient stiffness or rigidity that it can be moved to a position adjacent a stenosis to be treated by angioplasty. Achievement of this object is effected by providing an introducer composed of three relatively axially movable parts which are so arranged that the clinician can individually control the relative axial position of each of the parts.

Another object is to provide a guide for a dilatation catheter that preserves a substantially cross-sectional shape even when disposed in arcuate configuration at the intersection of two blood vessels. This object is achieved by the present invention because the wall of the outer tube is corrugated and is constructed such that it maintains a path having substantially circular cross-sectional shape even at rather severe curves.

The foregoing, together with other objects features and advantages, will be more apparent after referring to the following specification and the accompanying drawings.

BRIEF DESCRIPTION OF THE DRAWINGS

FIG. 1 is a view of an introducer according to the invention.

FIG. 2 is a fragmentary cross-sectional view at greatly enlarged scale showing certain details of construction of the device of FIG. 1.

FIGS. 3A–3C are schematic views of a blood vessel intersection and illustrate the procedure for positioning the device of the invention through the intersection.

DETAILED DESCRIPTION OF A PREFERRED EMBODIMENT

Referring more particularly to the drawing reference numeral 12 generally indicates a guide tube, reference numeral 14 generally indicates an intermediate telescoping introducer sized to fit interiorly of guide tube 12 and reference numeral 16 indicates a guide wire slidable interiorly of intermediate telescoping introducer 14. The three parts coact so that guide tube 12 can be positioned within a blood vessel at a position distally of a stenosis so as to define a clear passage for introduction of a dilatation catheter into the stenosis.

Guide tube 12 has an overall length of approximately 48 inches, more or less, and at the proximal end has a female Luered adapter 18 which affords engagement with the guide tube by a mechanism of the type described in the above cited *Journal of Cardiology* reference. Tube 12 is formed of heat shrinkable Teflon tubing which in one device designed in accordance with the invention has an inside diameter of about 0.049 inches. Throughout most of its length, guide tube 12 has a smooth interior and exterior surface, as indicated at 20 in FIG. 1. At the distal region thereof, guide tube 12 has a corrugated zone indicated at 22. The extent of corrugated zone in one device designed in accordance with the invention is about 5.9 inches and is confined to the distal region of the guide tube. Corrugated zone 22 includes a series of corrugations 24 which have substantially transversely extending annular wall portions 26. The annular wall portions serve to maintain the corrugated portion 22 in a circular condition even when the guide tube is disposed in an arcuate configuration within the intersection of two blood vessels. On the exterior of corrugated portion 22 there is a sleeve 28 that is heat shrunk on the exterior surface of the corrugated portion. Sleeve 28 imparts a degree of strength to the corrugated portion in an axial direction and presents a relatively smooth exterior surface which moves more easily through a blood vessel without adversely affecting the wall of the blood vessel. At its distal extremity, sleeve 28 extends slightly beyond the corrugated portion as indicated at 29 so that the transition between the relatively large diameter guide tube 12 and relatively small diameter intermediate telescoping introducer 14 is smooth in order to avoid impedance to introduction of the device through blood vessels or to adversely affect the internal wall of the blood vessel.

Intermediate telescoping sleeve 14 has an outside diameter that is small enough to pass freely through the passage defined by guide tube 12 but is sufficiently large as to impart a degree rigidity to the guide tube. For example, in one device designed in accordance with the invention, in which the inside diameter of guide tube 12 is 0.049 inches, the outside diameter of intermediate telescoping introducer 14 is about 0.045 inches. In the above mentioned design intermediate telescoping introducer 14 is formed of polyolefin tubing having a cylindrical outer cross-sectional shape. At its proximal end intermediate telescoping introducer has an enlargement 30 for affording manipulation of the introducer during angioplasty. Intermediate telescoping introducer 14 has a central passage or lumen 32 which is of circular cross-sectional shape and extends throughout the length of the intermediate telescoping introducer. In one device designed in accordance with the invention the ID of lumen 32 is about 0.022 inches. Intermediate telescoping introducer 14 has at its distal end a tapered portion 33 which is frusto conically shaped. The tapered portion facilitates axial movement of the intermediate telescoping introducer along a blood vessel without adversely affecting the interior surface of the wall of the blood vessel. Proximally of tapered portion 33 the intermediate telescoping introducer is provided with a radiopaque marker 34 which can be formed of gold or the like. Marker 34 is retained in place by a short length of heat shrink tubing 35, which has an outside diameter less than the inside diameter of guide tube 12.

Disposed within lumen 32 of the intermediate telescoping introducer is guide wire 16. In the above mentioned specific design in accordance with the invention, wherein the inside diameter of lumen 32 is about 0.022 inches, guide wire 16 has an outside diameter of about 0.018 inches. The clearance between the outside surface of the guide wire and the inside surface of lumen 32 is such as to afford free telescoping movement between the two parts. The proximal end of guide wire 16 is fitted with an enlargement 36 to afford both axially and rotative movement of the guide wire in lumen 32. Guide wire 16 can be formed of platinum or like material that has sufficient strength to be moved through a blood vessel, that has a sufficient degree of flexibility to follow the curvature of the blood vessel and that has sufficient malleability to be selectively deformed at the distal end. This selective deformation enables the clinician to control the direction of movement of the guide wire as it is moved in transversal of an intersection between two blood vessels, such deformation being indicated at 37.

The salutary advantages afforded by the present invention can be appreciated from the following description in connection with FIGS. 3A-3C. Before the apparatus of the invention is employed, a guiding catheter of relatively large diameter is introduced percutaneously as described in the above noted *Journal of Cardiology* reference. The relatively large diameter guiding catheter can typically be moved as far as the ascending aorta, the ostium of which is such as to prevent further advance of the guiding catheter. Thereafter the three relatively telescoping parts of the present invention are substantially axially aligned with one another and introduced through the guiding catheter. If undue resistance is encountered distally of the guiding catheter, the device of the present invention can be advanced by first extending the guide wire 16 outward followed by movement of intermediate telescoping introducer 14 distally along the guide wire and finally advancing the guide tube 12 along the intermediate telescoping introducer. With reference to FIG. 3A in which the left anterior descending artery is identified at A and the left circumflex coronary artery is indicated at C, guide tube 12 is seen positioned above the intersection of the two arteries. Advance to this point can ordinarily be readily achieved. Because the end 37 of guide wire 12 has been deformed, the guide wire can be manipulated into the entrance of circumflex artery C. After the wire has been advanced beyond the position shown in FIG. 3A to the approximate position shown in FIG. 3B, intermediate telescoping guide 14 is advanced over the guide wire and into the circumflex artery. The presence of tapered portion 33 at the distal end of the intermediate telescoping introducer facilitates movement through the blood vessel. After the intermediate telescoping introducer is positioned as in FIG. 3B, guide tube 12 is telescoped along the exterior surface of the intermediate telescoping introducer until the guide tube assumes the position seen in FIG. 3C. Because of the presence of sleeve 28 on the exterior of corrugated portion 22, substantial axial force can be applied to the corrugated portion of guide tube 12 without significant deformation of the guide tube. The presence of radially extending wall portions 26 with corrugated portion 22, the cross-sectional shape of the guide tube is maintained in a circular configuration notwithstanding the arcuate bend as seen in FIG. 3C. With the outer guide tube so positioned, guide wire 16 and intermediate telescoping introducer 14 are extracted from guide tube 12. Thereafter, a balloon catheter is introduced through the guide tube and can be positioned within a stenosis S with substantial facility. A low profile balloon catheter is employed to advance with the device of the invention. Unlike certain catheters that were previously used, a low profile catheter has no central lumen to accommodate a guide wire. Even without the guide wire within the balloon catheter, however, introduction is readily achieved because the balloon catheter is confined within the guide tube and axial force applied to the proximal end of the balloon catheter is translated through the intersection of the main artery at the circumflex artery because of such confinement. Thus the balloon catheter can be introduced into the stenosis and dilatation thereof can proceed.

To recapitulate it will be seen that the present invention provides a method for introducing a dilatation catheter into a stenosis within a blood vessel. The method involves providing an outer guide tube having a corrugated wall portion adjacent the distal extremity thereof, telescoping within the guide tube an intermediate introducer and telescoping within the intermediate introducer a guide wire. The three elements in substantial axial alignment are then positioned so that their distal end is proximally of a blood vessel intersection. Next the guide wire is advanced through the intersection, the intermediate telescoping introducer is telescoped over the guide wire and the guide tube is telescoped over the intermediate telescoping introducer. When the distal end of the guide tube is positioned adjacent the stenosis, the intermediate telescoping introducer and guide wire are removed and the dilatation catheter is introduced through the guide tube and into the stenosis. The balloon catheter can be introduced into severe stenoses located in the circumflex artery because the shaft of the balloon catheter is prevented from buckling by confinement within the guide tube of the present invention so as to afford transmission of substantial axial force from the proximal end of the catheter to the distal end at which the balloon is located.

Thus it will be seen that the present invention provides a balloon catheter introducing mechanism which facilitates introduction of a balloon catheter into severe stenoses even when they are located in the circumflex artery or other blood vessels that are oblique of the main artery. Because of the presence of corrugated wall portion 22 in the guide tube, the balloon catheter is confined as it traverses the arcuate part at an intersection of two blood vessels so that axial force applied to the proximal end of the balloon catheter is transmitted without significant decrease to the balloon as it is introduced into a stenosis.

Although one embodiment of the invention has been shown and described it will be apparent that other adaptations and modifications can be made without departing from the true spirit and scope of the invention.

What is claimed is:

1. Guiding apparatus for affording introduction of a balloon catheter into a stenosis in a blood vessel which is a branch extending at a substantial angle with respect to a main blood vessel comprising a guide tube having an outside dimension sized for entry into the blood vessel, said guide tube having a wall defining a passage having an inside dimension sized to afford introduction of the balloon catheter therethrough, said guide tube having a distal end and a proximal end, the wall of said guide tube in a zone adjacent the distal end thereof being circumferentially formed so that said guide tube can be curvilinearly disposed in a blood vessel while maintaining said passage in an open condition, an introducer tube having an outside dimension sized for entry into the passage in said guide tube, said introducer tube having an axial extent greater than said guide tube and having a distal end, said introducer tube having a centrally disposed lumen extending axially thereof, and a bendable aiming wire having a length greater than said introducer tube and disposed in said lumen for axial telescoping movement relative to said introducer tube, said introducer tube being telescopically movable within said guide tube passage and being removable therefrom to permit introduction of a balloon catheter through said passage, said aiming wire being adapted to be introduced into the branch blood vessel so that the introducer tube can follow the aiming wire into the branch blood vessel and the guide tube can follow the introducer tube.

2. Guiding apparatus according to claim 1 wherein said passage and the exterior of said introducer tube have substantially circular cross-sectional shapes.

3. Guiding apparatus according to claim 1 wherein the zone is provided with corrugations and a sleeve tightly circumscribing the exterior of the corrugations in the zone of said guide tube, said sleeve providing axial immobility to said zone and defining a relatively smooth exterior surface.

4. Guiding apparatus according to claim 3 wherein said sleeve extends to the distal extremity of said guide tube, said corrugated zone terminating proximally of said distal end to define a transition portion of reduced outside diameter to facilitate movement of said guide tube through a blood vessel.

5. Guiding apparatus according to claim 3 wherein said guide tube is formed of polytetrafluoroethylene and said sleeve is formed of polyolefin.

6. Guiding apparatus according to claim 1 wherein the distal end of said introducer tube has a tapered external portion that converges in a direction distally of said introducer tube for facilitating movement of said introducer through a blood vessel.

7. Guiding apparatus according to claim 6 including a radiopaque marker mounted adjacent the distal end of said introducer tube and a sleeve tightly circumscribing said marker and said introducer tube.

8. A method for positioning a dilatation catheter within a stenosis in a blood vessel comprising the steps of providing a bendable guide tube that defines a central passage having an inside dimension sized to receive the dilatation catheter therethrough, providing an introducer that is telescopically receivable in said passage, the introducer having a central lumen, installing an aiming wire in the lumen, placing the introducer in the guide tube, introducing the guide tube and introducer into a blood vessel, sequentially advancing the aiming wire, the introducer and the guide tube until the distal end of the guide tube is adjacent the stenosis, removing the introducer and aiming wire from the guide tube, inserting the dilatation catheter through the guide tube, and projecting the dilatation catheter beyond the distal end of the guide tube and into the stenosis.

9. In a dilatation catheter positioning apparatus for use in introducing a balloon dilatation catheter into a stenosis in a blood vessel which is a branch disposed at a substantial angle with respect to the main blood vessel, an outer guide tube having an outer dimension sized for entry into the main blood vessel, an inner guide tube slidably disposed in the outer guide tube and sized so that it is capable of entering the branch vessel, and a flexible guide wire slidably disposed in the inner guide tube and being capable of being directed to enter the blood vessel which is in a branch at a substantial angle with respect to the main blood vessel, the outer guide tube having a portion thereof near its distal extremity which is formed to give it greater flexibility while still retaining substantial rigidity in an axial direction so that the inner guide tube can be advanced over the guide wire by applying a pushing force to the distal extremity of the inner guide tube.

10. Apparatus as in claim 9 wherein said portion of said outer guide tube is provided with corrugations.

11. Apparatus as in claim 10 wherein a sleeve is disposed over the corrugations in said portion to provide a relatively smooth outer surface substantially co-extensive with the length of the portion having corrugations therein.

12. In a method for positioning a dilatation catheter within a stenosis in a branch blood vessel which is at a substantial angle with respect to a main blood vessel, inserting a guiding catheter into the main blood vessel, inserting a bendable guide tube into the guiding catheter, the bendable guide tube being sized to receive the dilatation catheter, introducing an introducer tube into the bendable tube, the introducer tube having an axially extending lumen therein, introducing a guide wire into the lumen of the introducer tube, advancing the guide wire in the blood vessel in such a manner so that it enters the branch blood vessel and at least approaches the stenosis in the blood vessel, advancing the introducer tube on the guide wire so that it also enters the branch blood vessel, advancing the bendable guide tube over the introducer tube so that it also extends into the branch vessel so that it is adjacent to the stenosis, removing the introducer tube and the guide wire from the bendable guide tube and inserting the dilatation catheter through the bendable guide tube and advancing it into the stenosis located in the branch blood vessel.

* * * * *